US008515154B2

(12) United States Patent
Scherübl et al.

(10) Patent No.: US 8,515,154 B2
(45) Date of Patent: Aug. 20, 2013

(54) VERIFICATION METHOD FOR REPAIRS ON PHOTOLITHOGRAPHY MASKS

(75) Inventors: Thomas Scherübl, Jena (DE); Matthias Wächter, Jena (DE); Hans Van Doornmalen, Veghel (NL)

(73) Assignee: Carl Zeiss SMS GmbH, Jena (DE)

( * ) Notice: Subject to any disclaimer, the term of this patent is extended or adjusted under 35 U.S.C. 154(b) by 550 days.

(21) Appl. No.: 12/754,218

(22) Filed: Apr. 5, 2010

(65) Prior Publication Data

US 2010/0254591 A1 Oct. 7, 2010

(30) Foreign Application Priority Data

Apr. 7, 2009 (DE) .......................... 10 2009 016 952

(51) Int. Cl.
*G06K 9/00* (2006.01)
(52) U.S. Cl.
USPC .................. 382/144; 382/151; 430/5; 430/11; 430/394
(58) Field of Classification Search
USPC .......................... 382/144–151; 430/5, 11, 394
See application file for complete search history.

(56) References Cited

U.S. PATENT DOCUMENTS

| 6,016,357 A | 1/2000 | Neary et al. |
| 7,331,033 B2 | 2/2008 | Feldman |
| 8,142,958 B2 * | 3/2012 | Holfeld .............................. 430/5 |
| 2008/0247632 A1* | 10/2008 | Boehm et al. ................. 382/144 |

OTHER PUBLICATIONS

German Search Report for Application No. 10 2009 016 952.0 dated Nov. 3, 2009.

* cited by examiner

*Primary Examiner* — Gregory J Toatley
*Assistant Examiner* — Iyabo S Alli
(74) *Attorney, Agent, or Firm* — Fish & Richardson P.C.

(57) ABSTRACT

A method for verifying repairs on masks for photolithography is provided. A mask fabricated based on a mask layout is inspected for defects, and the positions at which defects are found on the mask are stored in a position file. In a repair step, the defects are repaired and, for each repaired position, in a verification step, an aerial image of the mask is taken at that position and the aerial image is analyzed to determine whether at that position the mask meets tolerance criteria established for one or more selected target parameters, and if the tolerance criteria have been met, the repair is verified. The verification can include a) based on the position file, a desired structure is defined in the mask layout at the repaired position, b) an aerial image is simulated for the desired structure, c) the captured aerial image is compared with the simulated one, and d) based on the comparison, a decision is made as to whether the repair at that position is verified.

20 Claims, 2 Drawing Sheets

VERIFICATION METHOD FOR REPAIRS ON PHOTOLITHOGRAPHY MASKS

CROSS REFERENCE TO RELATED APPLICATION

Under 35 U.S.C. §119, this application claims the benefit of foreign priority of German Patent Application 10 2009 016 952.0, filed Apr. 7, 2009, the contents of which are hereby incorporated by reference in their entirety.

TECHNICAL FIELD

This document generally relates to verifying repairs on masks for photolithography.

BACKGROUND

Growth in the use of masks for photolithography, especially immersion photolithography, where structure sizes can be as small as 45 nm or less, has caused mask structures to become increasingly complex. Special design programs are used to produce the mask design, i.e., essentially the locations of the structures on the mask, convert it to a mask layout that incorporates lithographic requirements (e.g., the photoresist used, the light source used, the imaging scale), and store it in a file. The mask layout is the basis for the production of the mask. Due to the complexity of mask structures, the production costs of photolithography masks, especially those suitable for immersion lithography, are quite high. To prevent driving these costs still higher, defects or errors in the production process are repaired whenever possible.

In some examples, to find defects on masks, after the requisite production steps, the masks are checked for defects by using inspection systems. The inspection systems generate position files in which the positions where defects exist are stored. The position files may include a classification of the defects found at a given position according to predefined categories. The position files, in turn, serve as inputs for "mask repair systems," such as, for example, MeRiT® system, available from Carl Zeiss SMS GmbH. From the inspection system, the mask is routed to the mask repair system. In the mask repair system, the defect positions stored in the position file are navigated to, one by one, and an effort is made to repair the defect, for example by depositing or removing material.

After all the defects have undergone repairs, the result of the repair is verified for each defect. The verification should take place under conditions that reflect the imaging conditions in the photolithography scanner as closely as possible. In particular, this calls for optical qualification under the same lithographically relevant conditions as in the photolithography scanner. For example, the wavelength, the numerical aperture and the illumination setting (such as dipole or quadrupole illumination) of the imaging system used for the verification are matched to those of the photolithography scanner. The verification can, for example, be performed using an emulation imaging system that emulates a photolithography scanner, in which an image of the mask, instead of being displayed in reduced form on the photoresist on a wafer (as in a photolithography scanner), is displayed in magnified form on a spatially resolving detector, for example a charge coupled device (CCD) camera. One such simulation imaging system is AIMS® system, available from Carl Zeiss SMS GmbH. This machine navigates to the repaired position and takes a corresponding image of the repaired site, known as an aerial image (equivalent to an image taken in a photoresist layer above the wafer), on the mask at the repaired position.

In some examples, whether the repair was successful and the mask can thus be verified is determined by manual comparison with a structure at another point on the mask that is identical but has no defect, and thus did not have to be repaired. Tolerance criteria are defined for these target parameters, and consideration may also be given to, for example, the behavior and/or the values of the target parameters at the identical, unrepaired site. Based on the aerial image, compliance with the tolerance criteria is then checked using evaluation algorithms. If the tolerance criteria are met, then any deviations from the ideal value are within tolerance, the repair at the position under examination is verified, and the position can be marked accordingly in the position file or, alternatively, deleted from the position file. If the tolerance criteria are not met, then the position can also be marked accordingly in the position file so it can undergo another repair.

The comparison and the verification of repairs can be done manually: a user looks for an identical, unrepaired site near the repaired site and analyzes and compares the two images. This is time-consuming, especially in cases where a similar structure can be found only outside the image area of the emulation imaging system.

Another prerequisite for this type of verification is that the mask needs to have similar structures that can be used to make the comparison. In the case of masks for logic circuits, however, this condition is not always met. The masks for logic circuits tend to feature a large number of structures, each of which occurs only once. In this case it is difficult to achieve relatively precise verification of repairs, and an approximate verification by reference to similar structures is performed.

SUMMARY

In general, in one aspect, a method for verifying repairs on masks is provided. The method includes, in an inspection step, a mask fabricated on the basis of a mask layout is inspected for defects, and the positions at which defects are found on the mask are stored in a position file. In a repair step, the defects are repaired and, for each repaired position, in a verification step, an aerial image of the mask is taken at that position and the aerial image is analyzed to determine whether at that position the mask meets tolerance criteria established for one or more selected target parameters, and if the tolerance criteria are met, the repair is verified. The verification includes: a) based on the position file, a desired structure is defined in the mask layout at the repaired position, b) an aerial image is simulated for the desired structure, c) the captured aerial image is compared with the simulated one, and d) based on the comparison, a decision is made as to whether the repair at that position is verified.

Implementations may include one or more of the following features. The data stored in the mask layout can be made available to the repair system and the emulation imaging system. The position file, to which data concerning the type of repair performed at each position can also be added during the repair step, is used to find the desired structure, which represents the ideal structure with no defects, in the mask layout data. The desired structure is then used as the starting point for an optical simulation to simulate an aerial image of the kind that can be generated in the emulation imaging system. The simulation need not be limited to one aerial image, and can yield a stack of images simulated for various heights above the wafer surface. Such stacks of aerial images can also be taken with the emulation imaging system.

The input parameters for the optical simulation can be the optical settings as used in the emulation imaging system, such as the numerical aperture, the illumination settings, and the wavelength. It is also possible to use other data from other measuring instruments, for example atomic force microscopes and scanning electron microscopes, for determining the critical dimension, or phase measurement devices, which are used to determine the phase distribution in the exposure light on the surface of the wafer or CCD. It is also possible to take specific instrument parameters into account, for example the aberrations of the emulation imaging system.

The aerial image can be simulated by Fourier transformation of the desired structure or by use of rigorous simulation. One example of a suitable rigorous simulator is the SolidE®, available from Synopsys GmbH. Other parameters that increase the accuracy of the simulation in order to generate a realistic aerial image can also be taken into account.

Although the target parameters, such as the critical dimension and the process window, can be selected globally for the entire mask, in some examples the target parameters can be selected as a function of the desired structures. This can be done by specifying or selecting the target parameters specifically for defined regions of the desired structure, such as surfaces or certain geometrical shapes, which are specified by using local coordinates X, Y, Z. The target parameter can also relate to behavior in a defocused plane. This is a practical choice, for example, when an image stack is being simulated or captured and the target parameter is the process window. Other target parameters can include, for example, the transmission, the exposure latitude, and the normalized image log slope (NILS). The list of parameters is not limited to those described above, and other target parameters can also be selected.

Each of the target parameters can be assigned a tolerance criterion, which is usually derived from the lithographic tolerances, i.e., the tolerances that apply in the case of wafer exposure in a photolithography scanner using a given photoresist.

The captured aerial image can be compared with the simulated one. This examination can be performed visually by an observer. However, to simplify the comparison, the two aerial images, i.e., the simulated aerial image and the captured aerial image, can be compared directly. For this purpose, they are first correlated with each other. The two images can be aligned with each other so that like structures overlap each other when they are virtually superimposed, the superimposition normally being done pixel by pixel if the images have the same resolution, and if not, with the aid of interpolation algorithms. The correlation can then be performed directly on the basis of the two aerial images. Another option is to first establish a threshold value for the intensity on the basis of a desired critical dimension, and then to use this intensity threshold to generate what is known as a "contour plot". The correlation can then be performed on the basis of the contour plot.

If the images are correlated, then they are subtracted from each other. In the ideal case, the two images are identical, i.e., the simulated structure matches the repaired structure, and the repair is therefore nearly perfect. Immediate verification of the repair can take place in this case. The differential image thus contains no information. For example, given a pixel that can assume values of 0 (black) to 255 (white) on a gray scale, then in this case the differential image would be entirely black or, on an inverted color scale, entirely white.

In some examples, however, the captured aerial image and the simulated aerial image differ in content, so subtracting one of the images from the other results in an image that presents observable regions where the two images differ from each other. This is the case, for example, when the simulation of the desired structure yields a regularly shaped structure, for example a line, but in the actually captured aerial image, the line shows thickenings and/or thinnings caused by the repair. These information-containing regions can be analyzed on the basis of the captured aerial image. The measured aerial image can be used to determine the lithographically relevant target parameters, preferably for those regions where discrepancies are present, and these parameters are then analyzed to see whether the predefined tolerance criteria are met. Based on the comparison, a decision can be made as to whether the repair at that position is verified, which is the case if the tolerance criteria are met. If the deviation is greater and is outside the tolerance, the defect at that position can be specially marked. This marking can also be stored, as a function of position, in the position file. Sometimes the defect cannot be repaired, but it is generally useful to repeat the repair step and the ensuing verification step for unrepaired defects, so that the defects are iteratively eliminated. Another repair action may be necessary during the second repair step. For example, if too much material was deposited during the first repair step, then some of it can be removed during the second repair step. Another option is to add optical proximity correction (OPC) structures.

The analysis of the differential image can be performed by a user, but automatic image analysis, and thus automatic comparison, is practical and advantageous for efficient execution. This can be done by using image processing algorithms. It is advantageous in this case to establish a threshold value and to analyze or cause to be analyzed only the regions in which the amount of the difference between the captured and simulated aerial images is above the threshold, for each pixel in the images. The threshold value can be broadened to the effect that only regions that encompass a certain number of contiguous pixels whose difference values are above the threshold value are analyzed. This has the advantages that noise in the image is suppressed and that only regions that are relevant are represented or analyzed.

In the case of automatic execution, a check can be performed to determine whether the mask, in those regions, meets the predefined tolerance criteria for one or more selected target parameters. If a target parameter is outside a predefined tolerance range, then, for example, an output can be produced indicating that the repair was not successful and may have to be repeated. A corresponding data item can also be stored automatically in the appropriate position file. To complete the automatic analysis, the position file can then be analyzed to determine whether the defects have not been repaired, and the mask can be automatically routed to the repair system, which can use the data from the position file and proceed with a suitable repair.

One problem that can arise, especially in the case of very small mask structures, is that the structures written by a mask writer, which may operate by using electron beam lithography, may exhibit deviations from the desired structure specified in the mask layout. The size of the electron beam during the writing of the mask may result in "roundings" or smears on the real mask, for example at edges and corners of the mask structures. In the case of smaller structures or optical proximity correction structures, the smearing can affect the aerial image, and thus also the image transferred to the wafer. To register the effect of the mask writer in the simulated image, in some examples, before the desired structure is specified, the structures stored in the mask layout are adapted to the structure generated by a mask writer. This "rendering," as it is known (which is implemented, for example, as an option in the control system of the McRiT® system), generates the smears or roundings described above, thus yielding a mask layout that is substantially identical to the actual mask written by the mask writer. The modified mask layout is then searched for the desired structure on the basis of the position file, and the simulation is performed with the desired structure as the starting structure.

In some examples, the method is modified so that a second, identical structure is searched for automatically or manually in the mask layout, and the emulation imaging system then navigates to this identical structure and takes an aerial image of it. The comparison then takes place, not between a simulated aerial image and an actually captured aerial image, but between two actually captured aerial images. These images are properly correlated so that the structures are congruent. The rest of the comparison follows analogously to the method as described above.

It is understood that the features that have been recited above can be used not only in the stated combinations, but also in other combinations or individually, without departing from the scope of the present invention.

DESCRIPTION OF DRAWINGS

The invention is described exemplarily in more detail below with reference to the appended drawings.

DETAILED DESCRIPTION

Figure 1:
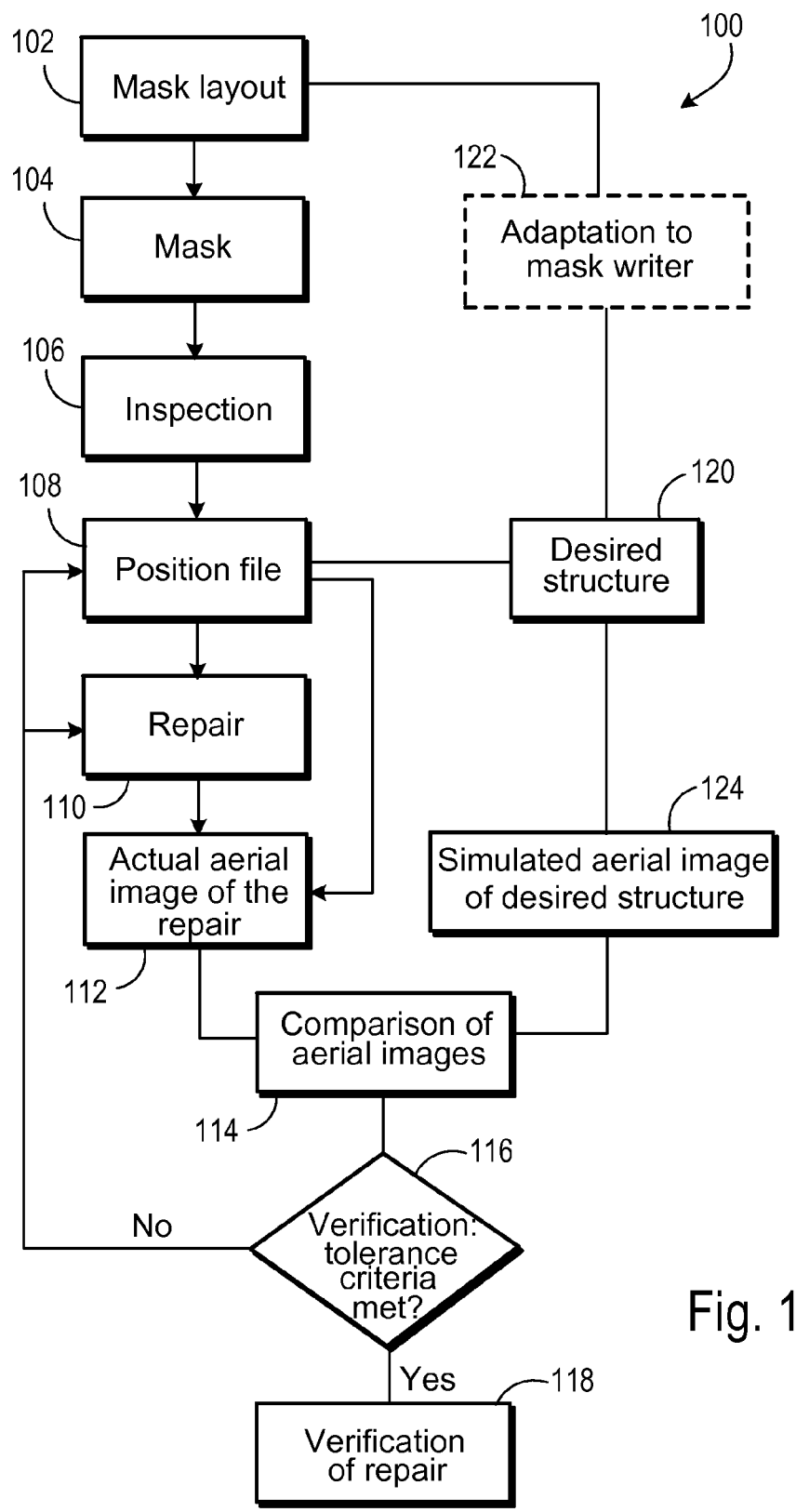
FIG. 1 is a flow diagram of a process for verifying repairs on a mask.

FIG. 1 shows an example process 100 for verifying repairs on masks for photolithography. Starting with a mask layout 102, a mask is fabricated 104, for example by electron beam lithography. The mask is inspected for defects in an inspection step 106, for example in an inspection system. The positions at which defects are found on the mask are stored in a position file 108, for example, in a format that can be accessed by all the connected systems, such as inspection, mask repair, emulation imaging, and simulation systems. In a repair step, the defects are repaired consecutively 110. For each repaired position, the type of repair can optionally be stored in the position file, which can additionally contain information concerning the nature of the defect, for example, a defect classification.

For each repaired position, in a verification step, an aerial image of the mask is taken at that position 112 (the aerial image shows only the portion of the mask at that position and its surroundings), and it is then determined (for example, by comparison of captured and simulated images 114), for one or more selected target parameters, whether predefined tolerance criteria for those parameters have been met 116. If the tolerance criteria are met, the repair is verified 118; otherwise, a notation to that effect can be made in the position file and the mask can be routed for re-repair and subsequent verification at that position.

Examples of target parameters that can be used include the critical dimension, the process window, the transmission, the exposure latitude (EL), the normalized image log slope (NILS), and/or other parameters from the aerial image. The selection of one or more target parameters can depend on the type of structure of the mask at the location where a defect is being repaired.

The number of aerial images taken need not be limited to one; it is also possible to generate stacks of aerial images for different heights above the wafer, which can be partially defocused. This can be useful when, for example, the process window is selected as a target parameter.

As part of the verification performed during the verification step, based on the position file a desired structure (or target structure) is defined based on the mask layout at the repaired position 120. Optionally, as signified by the dashed box in the flow chart, before the desired structure is defined, the mask layout can be adapted to a structure generated by a mask writer 122. The structure takes into account of the effects generated by the mask writer, such as roundings or smears on the mask at edges and corners of the mask structure. This permits a more realistic description of the actual structures and is advantageous in the case of small mask structures, where deviations from the design structure are noticeable, owing to the size of the electron beam used for electron beam lithography. An aerial image is simulated for the (optionally modified) desired structure 124, for example by Fourier transformation or Kirchhoff transformation of the desired structure, or by rigorous simulation, for which known tools can be used, such as, for example, the SolidE® program from Synopsys GmbH. The simulated aerial image is compared with the captured aerial image 114, for example using AIMS® tool, from Carl Zeiss SMS GmbH. Based on the comparison, a decision is made as to whether the repair at that position is verified 116.

This comparison can be done visually, but for a simplified analysis or a simplified comparison, which can be performed either manually or automatically, it is advantageous first to correlate the two aerial images with each other, i.e., to align counterpart structures with each other so that they show up as congruent in the superimposition, and then to subtract one image from the other image (for example, subtract the simulated aerial image from the captured aerial image). The analysis can then be limited to the regions where the simulated and captured aerial images differ from each other. Conformance with the tolerance criteria can be analyzed only for those regions, based on the captured aerial image. The target parameters need not be selected globally for the entire mask, but can be defined or selected specifically as a function of the desired structures, for example, as a function of the regions in which the two aerial images differ from each other.

A threshold value can be established for the subtraction operation so that during the differential imaging, only the regions or pixels are marked in which the difference between the two aerial images is above the threshold value. This prevents image noise. In addition, the regions that do not contain a given minimum number of contiguous pixels can be left out of consideration.

Figure 2:
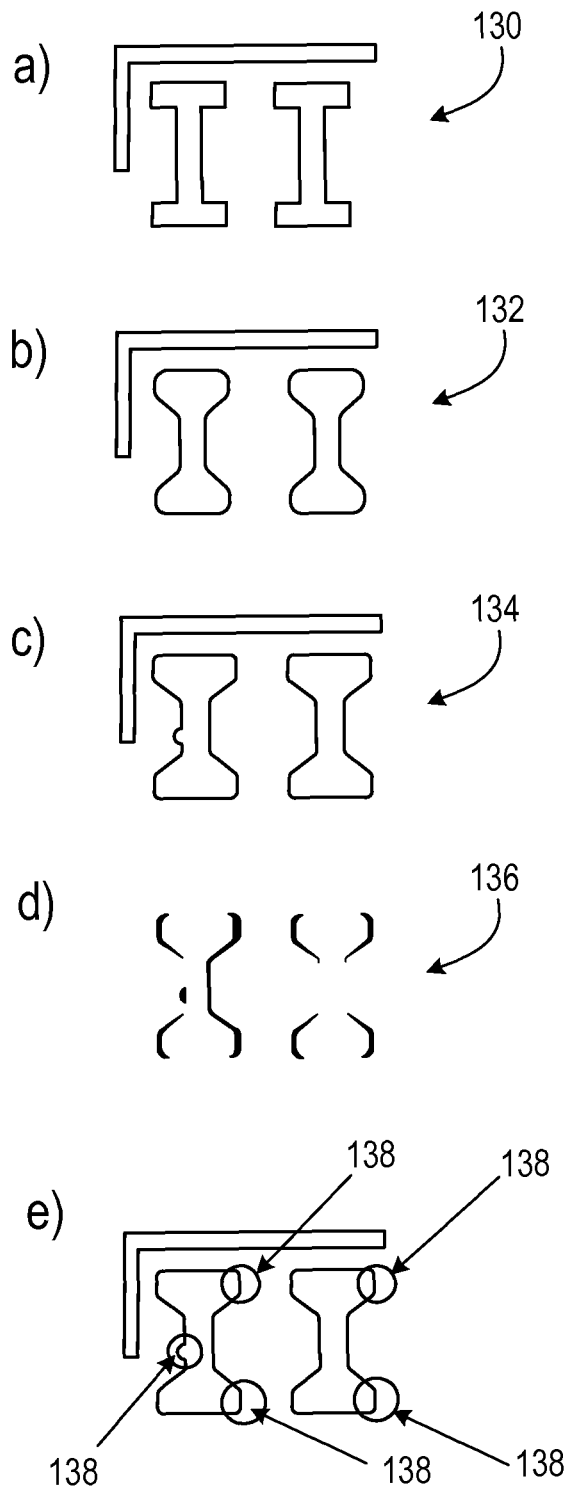
FIGS. 2a to 2e show an exemplary comparison performed during a verification step.

FIGS. 2a to 2e illustrate the procedure for selecting the regions in which the target parameters are to be checked for verification purposes, to see whether they conform to their tolerance criteria. In this example, the parameter of interest here is the critical dimension, which corresponds to the spatial extent of each structure. FIG. 2a shows a structure 130 as it appears in a mask layout at a position occupied by a repaired site. The structure 130 illustrated in FIG. 2a thus represents a desired structure. The structure 130 serves as an input for the optical simulation, it being understood that the structure 130 can still be modified to accommodate the effects of the mask writer.

The result of the optical simulation, the simulated aerial image 132, is shown in FIG. 2b. As illustrated in FIG. 2c, an aerial image 134 of the actual mask is taken at the same position, for example using the AIMS® emulation imaging system, which is used to emulate a photolithography scanner.

The aerial images 132, 134 illustrated in FIGS. 2b and 2c, respectively, are now correlated, i.e., aligned with each other, so that similar structures lie one on top of the other. A differential image 136 is generated, that is, the simulated image is subtracted from the actually captured aerial image.

The differential image 136 is shown in FIG. 2d. Regions in which the simulated aerial image 132 and the captured aerial image 134 differ from each other are clearly visible. A threshold value can be defined so that only the regions in which the difference is above the threshold value are shown. Only the regions are analyzed on the basis of the captured aerial image, the target parameters and the tolerance criteria being specifically selected and defined for the regions 138 of the captured aerial image that are identified in FIG. 2e. The evaluation to assess conformance with the tolerance criteria can be performed automatically, for example, by using programs designed for this purpose.

The above-described method provides an efficient and time-saving way of verifying repairs on masks. The uncertainties that can arise when structures are present only once on the mask can be reduced. The verification process involved can be completely or partially automated.

The features described above related to processing of data, such as simulation of aerial image of desired structure, comparison of simulated and captured aerial images, and verification of whether the tolerance criteria are met, can be implemented in digital electronic circuitry, or in computer hardware, firmware, software, or in combinations of them. The features can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output.

The described features related to processing of data can be implemented advantageously in one or more computer programs that are executable on a programmable system including at least one programmable processor coupled to receive data and instructions from, and to transmit data and instructions to, a data storage system, an input device, and an output device. A computer program is a set of instructions that can be used, directly or indirectly, in a computer to perform a certain activity or bring about a certain result. A computer program can be written in any form of programming language (e.g., Fortran, C, C++, Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. A computer may include a processor for executing instructions and one or more memories for storing instructions and data. Generally, a computer will also include, or be operatively coupled to communicate with, one or more mass storage devices for storing data files; such devices include magnetic disks, such as internal hard disks and removable disks, magneto-optical disks, and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

A number of implementations have been described. Nevertheless, it will be understood that various modifications may be made. For example, elements of one or more implementations may be combined, deleted, modified, or supplemented to form further implementations. As yet another example, the logic flow depicted in FIG. 1 does not require the particular order shown, or sequential order, to achieve desirable results. In addition, other steps may be provided, or steps may be eliminated, from the described flows, and other components may be added to, or removed from, the described systems.

For example, the target parameters that are selected for determining whether tolerance criteria are met can be different from those described above. The mask can be fabricated by methods other than electron beam lithography. The threshold value that is used for the subtraction operation does not have to be constant throughout the image. For example, the threshold value can vary depending on the feature sizes. When several images are taken at different heights above the wafer surface, different threshold values can be used for images taken at different heights. The iteration process for repairing defects can be terminated based on predetermined conditions, such as setting a maximum number of repair cycles.

What is claimed is:

1. A method for verifying repairs on masks for photolithography, the method comprising:
   inspecting a mask for defects, the mask being fabricated based on a mask layout;
   storing positions at which the defects are found on the mask in a position file;
   repairing the defects and, for each position of a repaired defect,
      taking an aerial image of the mask at the position of the repaired defect,
      analyzing the aerial image to determine whether at that position the mask meets tolerance criteria established for one or more selected target parameters, and
      verifying the repair if the tolerance criteria are met, the verifying comprising:
         based on the position file, determining a desired structure in the mask layout at the position of the repaired defect,
         simulating an aerial image for the desired structure,
         comparing the captured aerial image with the simulated image, and
         based on the comparison, determining whether the repair at that position is verified.

2. The method of claim 1, wherein simulating the aerial image comprises simulating the aerial image by at least one of performing a Fourier transformation of the desired structure or a rigorous simulation of the desired structure.

3. The method of claim 1, wherein comparing the captured aerial image with the simulated image comprises correlating the captured aerial image and the simulated image, subtracting one image from the other image, and analyzing the regions in which the simulated and the captured aerial images differ from each other for conformance with the tolerance criteria, based on the captured aerial image.

4. The method of claim 3, comprising selecting the target parameters as a function of the desired structures.

5. The method of claim 4, wherein selecting the target parameters as a function of the desired structures comprises selecting the target parameters as a function of the regions of the desired structures in which the simulated and the captured aerial images differ from each other.

6. The method of claim 3, wherein analyzing the regions comprises analyzing only the regions in which the amount of the difference between the simulated and the captured aerial images is above a specified threshold value.

7. The method of claim 1, wherein determining the desired structure comprises configuring the desired structure based on the mask layout, taking into account of effects generated by a mask writer.

8. The method of claim 1, wherein analyzing the aerial image to determine whether at that position the mask meets tolerance criteria established for one or more selected target parameters comprises
analyzing the aerial image to determine whether at that position the mask meets tolerance criteria established for at least one of critical dimension, process window, transmission, exposure latitude, or normalized image log slope.

9. The method of claim 1, comprising performing repairing the defect and verifying the repair again for a repaired defect that does not meet the tolerance criteria.

10. A method for verifying repairs on a mask for photolithography, the method comprising:
repairing defects on a mask that is fabricated according to a mask layout;
for each repaired defect,
capturing an aerial image of the mask at a position of the repaired defect,
simulating an aerial image for a desired structure in the mask layout at the position of the repaired defect, and
verifying the repair, including comparing the captured aerial image and the simulated aerial image to determine whether at the position of the repaired defect the mask meets tolerance criteria established for one or more selected target parameters.

11. The method of claim 10 in which simulating the aerial image comprises simulating the aerial image by at least one of performing a Fourier transformation of the desired structure or a rigorous simulation of the desired structure.

12. The method of claim 10 in which comparing the captured aerial image with the simulated aerial image comprises correlating the captured aerial image and the simulated aerial image, subtracting one image from the other image, and analyzing the regions in which the simulated and the captured aerial images differ from each other for conformance with the tolerance criteria.

13. The method of claim 12, comprising selecting the target parameters as a function of the desired structures.

14. The method of claim 12 in which analyzing the regions comprises analyzing only the regions in which the amount of the difference between the simulated and the captured aerial images is above a predetermined threshold value.

15. The method of claim 10 in which simulating the aerial image comprises simulating an aerial image for a target structure at a position in the mask layout that corresponds to a position of the repaired defect, taking into account effects generated by a mask writer.

16. The method of claim 10 in which analyzing the aerial image to determine whether at that position the mask meets tolerance criteria established for one or more selected target parameters comprises
analyzing the aerial image to determine whether at that position the mask meets tolerance criteria established for at least one of critical dimension, process window, transmission, exposure latitude, or normalized image log slope.

17. A method for removing defects from a photolithography mask, the method comprising:
iteratively repairing defects on a mask for photolithography,
comparing captured aerial images of the repaired defects and corresponding simulated aerial images of desired structures, and
verifying that the repairs meet tolerance criteria established for one or more selected target parameters,
wherein for each iteration after the first iteration, the repairing and verifying are repeated on defects for which the tolerance criteria are not met in a previous iteration, and wherein the simulated aerial images of the desired structures are determined after the repairing in the first iteration and the simulations are performed at the positions of the defects.

18. The method of claim 17 in which the mask is fabricated according to a mask layout, and for each defect, the simulated aerial image comprises a simulated aerial image for a corresponding structure in the mask layout, taking into account effects generated by a mask writer that writes the mask according to the mask layout.

19. The method of claim 18 in which the effects generated by a mask writer comprise at least one of roundings or smears on the mask structure.

20. The method of claim 17 in which comparing captured aerial images of the repaired defects and corresponding simulated aerial images of desired structures comprises comparing captured aerial images of the repaired defects captured at various heights above the wafer surface and corresponding simulated aerial images of desired structures simulated for various heights above the wafer surface.

* * * * *

UNITED STATES PATENT AND TRADEMARK OFFICE
CERTIFICATE OF CORRECTION

PATENT NO. : 8,515,154 B2
APPLICATION NO. : 12/754218
DATED : August 20, 2013
INVENTOR(S) : Thomas Scherübl, Matthias Wächter and Hans Van Doornmalen Page 1 of 1

It is certified that error appears in the above-identified patent and that said Letters Patent is hereby corrected as shown below:

In the Specification

<u>Column 5</u>
Line 1, delete "McRit®" and insert -- MeRit® --

Signed and Sealed this
Fifth Day of November, 2013

Teresa Stanek Rea
*Deputy Director of the United States Patent and Trademark Office*